(12) United States Patent
Masumoto

(10) Patent No.: US 9,117,287 B2
(45) Date of Patent: Aug. 25, 2015

(54) IMAGE ANALYSIS APPARATUS, METHOD, AND PROGRAM

(71) Applicant: FUJIFILM Corporation, Tokyo (JP)

(72) Inventor: Jun Masumoto, Tokyo (JP)

(73) Assignee: Fujifilm Corporation, Tokyo (JP)

(*) Notice: Subject to any disclaimer, the term of this patent is extended or adjusted under 35 U.S.C. 154(b) by 0 days.

(21) Appl. No.: 14/489,529

(22) Filed: Sep. 18, 2014

(65) Prior Publication Data

US 2015/0005659 A1    Jan. 1, 2015

Related U.S. Application Data

(63) Continuation of application No. PCT/JP2013/001640, filed on Mar. 13, 2013.

(30) Foreign Application Priority Data

Mar. 23, 2012  (JP) ................................ 2012-066598

(51) Int. Cl.
*G06K 9/00* (2006.01)
*G06T 7/20* (2006.01)
(Continued)

(52) U.S. Cl.
CPC . *G06T 7/20* (2013.01); *A61B 5/055* (2013.01); *A61B 5/091* (2013.01); *A61B 5/113* (2013.01);
(Continued)

(58) Field of Classification Search
CPC ...... A61B 6/5217; A61B 6/463; A61B 5/087; A61B 5/091; A61B 5/113; G06T 2207/30061; G06T 2207/30064; G06T 7/0016
USPC ......................................................... 382/131
See application file for complete search history.

(56) References Cited

U.S. PATENT DOCUMENTS

| 5,776,071 A | 7/1998 | Inukai et al. |
| 2004/0109595 A1* | 6/2004 | Luo et al. ...................... 382/132 |

(Continued)

FOREIGN PATENT DOCUMENTS

| JP | 9-294728 A | 11/1997 |
| JP | 2005-28121 A | 2/2005 |

(Continued)

OTHER PUBLICATIONS

International Search Report (ISR) (PCT Form PCT/ISA/210), in PCT/JP2013/001640, dated Jul. 9, 2013.

(Continued)

*Primary Examiner* — Ali Bayat
(74) *Attorney, Agent, or Firm* — McGinn IP Law Group, PLLC

(57) ABSTRACT

An image analysis apparatus that analyzes, based on a series of three-dimensional images of lungs at different time phases, a three-dimensional distribution of ventilation volume of the lungs, includes a lung region extraction unit that extracts a lung region from each of the three-dimensional images; an alignment unit that aligns the lung regions between the series of three-dimensional images and calculates a displacement vector field in the lung region; a function calculation unit that calculates a local ventilation volume function representing a temporal change in ventilation volume at each point in the displacement vector field in each of the three-dimensional images based on the displacement vector field; and a quantification unit that quantifies a difference between the local ventilation volume function and a benchmark ventilation volume function serving as a reference and calculates a quantitative value representing the difference.

14 Claims, 7 Drawing Sheets

(51) Int. Cl.
- *A61B 6/03* (2006.01)
- *A61B 6/00* (2006.01)
- *A61B 5/055* (2006.01)
- *A61B 5/113* (2006.01)
- *G06T 7/00* (2006.01)
- *A61B 5/091* (2006.01)

(52) U.S. Cl.
CPC . *A61B 6/032* (2013.01); *A61B 6/50* (2013.01); *A61B 6/5217* (2013.01); *G06T 7/0028* (2013.01); *A61B 6/037* (2013.01); *A61B 6/461* (2013.01); *G06T 2207/10081* (2013.01); *G06T 2207/10084* (2013.01); *G06T 2207/10088* (2013.01); *G06T 2207/30061* (2013.01)

(56) References Cited

U.S. PATENT DOCUMENTS

| | | | |
|---|---|---|---|
| 2008/0009683 A1 | 1/2008 | Bogoni et al. | |
| 2013/0156158 A1* | 6/2013 | Noji et al. | 378/62 |
| 2013/0156267 A1* | 6/2013 | Muraoka et al. | 382/103 |

FOREIGN PATENT DOCUMENTS

| | | |
|---|---|---|
| JP | 2008-253293 A | 10/2008 |
| JP | 2009-153677 A | 7/2009 |
| JP | 2010-268979 A | 12/2010 |
| WO | WO 2012/026146 A1 | 3/2012 |

OTHER PUBLICATIONS

V. Boldea et al., "Lung Deformation Estimation with Non-rigid Registration for Radiotherapy Treatment", Proceedings of MICCAI, vol. 2878, pp. 770-777, 2003.

R. Werner et al., "Modeling Respiratory Lung Motion—a Biophysical Approach using Finite Element Methods", Proc. of SPIE, vol. 6916, pp. 69160N-1-69160N-11, 2008.

H. Kitaoka, "A 4D Model Generator of the Human Lung", Forma, vol. 26, pp. 19-24, 2011.

K. Du et al., "Registration-Based Measurement of Regional Expiration Volume Ratio Using Dynamic 4DCT Imaging", IEEE International Symposium on Biomedical Imaging, pp. 424-428, 2011.

Japanese Office Action dated Mar. 31, 2015 with a partial English translation thereof.

* cited by examiner

IMAGE ANALYSIS APPARATUS, METHOD, AND PROGRAM

CROSS-REFERENCE TO RELATED APPLICATIONS

This application is a Continuation of PCT International Application No. PCT/JP2013/001640 filed on Mar. 13, 2013, which claims priority under 35 U.S.C. §119 (a) to Japanese Patent Application No. 2012-066598 filed on Mar. 23, 2012. Each of the applications is hereby expressly incorporated by reference, in its entirety, into the present application.

BACKGROUND OF THE INVENTION

1. Technical Field

The present invention relates to an image analysis apparatus and method for analyzing a three-dimensional distribution of ventilation volume of lungs using three-dimensional images representing motion of the lungs during respiration, and a program for causing a computer to perform the image analysis method.

2. Background Art

Recently, high quality three-dimensional images are used in image diagnosis with the advancement of medical equipment (e.g., multi-detector CT, hereinafter referred to as multi-slice CT, and the like). In the multi-slice CT, a plurality of rows of detectors for detecting X-ray is provided and a plurality of tomographid images can be obtained at a time by one rotation of the rows of detectors around a human body. The number of detectors has been increased exponentially by the technological advancement, and recently a multi-slice CT with a maximum of 320 rows has been used. The time required for the detectors to make one rotation around a human body is about 0.35 seconds and the imaging range in an axis direction of the human body extends over to 16 cm. Consequently, in the regions, such as head, heart, and the like, it is possible to obtain a plurality of three-dimensional images in time series at a short time interval. By displaying, in time series order, an organ of interest included in the three-dimensional images obtained in time series as described above, it is possible to observe the motion of an organ, such as a heart or the like, like seeing a moving picture. It is also possible to observe, in the head and the heart, how a contrast agent or the like circulates through the body in the three-dimensional images.

In the meantime, the amount of radiation received by the subject is increased with the increase in the imaging range and the number of imaging times, but developments of image reconstruction algorithms that allow high quality images to be obtained with a less amount of radiation have been conducted in manufactures of modalities, such as imaging equipment. Consequently, imaging over a wide range with a prolonged time, which required a large amount of radiation in the past, has also been conducted.

With respect also to lungs, it is becoming possible by such advancement in modalities to obtain three-dimensional images of the entire lung region (about 30 cm) in time series at a short time interval during a series of respiration cycle of inhaling largely and exhaling. This allows the motion of the lungs due to respiration to be observed like seeing a moving image.

In the meantime, bronchial asthma and lung emphysema may be cited as respiratory diseases. Heretofore, with respect to these diseases, spirometers (spirometry) or nuclear medicine studies, such as lung scintigraphy of SPECT, have been used to check the ventilation volume of the lungs. Here, the spirometry measures the volume of breath exhaled by the subject and the exhaling time, and is recommended as tests for diagnosing lung diseases such as COPD (Chronic Obstructive Pulmonary Disease) and the like. The spirometry may obtain a ventilation volume of the entire lungs and the ventilation curve (vital capacity curve), but is unable to check which portion of the lungs has a reduced ventilation volume. The SPECT scan may visualize the state of ventilation with respect to each region, but is unable to obtain detailed information due to relatively poor image quality. Further, it has a problem that the amount of radiation received by the patient is increased as it is necessary to inject a radioactive material into the body of the patient.

Consequently, a method that extracts lung regions from CT images of two phases of exhalation and inhalation, aligns the extracted lung regions using a non-rigid registration method and obtains a displacement vector field in the lung region, and calculates a local ventilation volume of the lungs by calculating a divergence of the displacement vector field is proposed (refer to Japanese Unexamined Patent Publication No 2005-028121).

Further, a method that disposes an air passage in each of three-dimensional time series images representing lung motion, extracts a three-dimensional grid point between air passages in each three-dimensional image, and measures a spread of tracheomalacia by measuring the volume of the extracted point is proposed (refer to U.S. Patent Application Publication No. 20080009683).

DISCLOSURE OF THE INVENTION

As the method described in Japanese Unexamined Patent Publication No 2005-028121 calculates a local ventilation volume of lungs from CT images in two phases of exhalation and exhalation, the method cannot check a temporal change in ventilation volume which shows from which portion of the lungs air is started to be taken in and from which portion air exits. The method described in U.S. Patent Application Publication No. 20080009683 may check the three-dimensional lung motion during respiration and a spread of tracheomalacia, but cannot confirm the ventilation volume of the lungs.

The present invention has been developed in view of the circumstances described above, and it is an object of the present invention to enable confirmation of a local abnormality of lungs along with a three-dimensional motion of lungs during respiration.

An image analysis apparatus according to the present invention is an apparatus that analyzes, based on a series of three-dimensional images of lungs at different time phases, a three-dimensional distribution of ventilation volume of the lungs, the apparatus including:

a lung region extraction means that extracts a lung region from each of the three-dimensional images;

an alignment means that aligns the lung regions between the series of three-dimensional images and calculates a displacement vector field in the lung region;

a function calculation means that calculates a local ventilation volume function representing a temporal change in ventilation volume at each point in the displacement vector field in each of the three-dimensional images based on the displacement vector field; and a quantification means that quantifies a difference between the local ventilation volume function and a benchmark ventilation volume function serving as a reference and calculates a quantitative value representing the difference.

As for the "series of three-dimensional images of lungs at different time series", any type of images may be used as long as they are obtained by imaging the chest region, including the lungs, of the same subject in series at a short time interval and capable of reproducing lung motion due to respiration by being displayed in time series order. More specifically, three-dimensional images generated from CT images or MR images may be used In the image analysis apparatus according to the present invention, the quantification means may be a means that calculates a difference function representing a difference between the local ventilation volume function and the benchmark ventilation volume function as the quantitative value.

Further, in the image analysis apparatus according to the present invention, the quantification means may be a means that calculates a difference function representing a difference between the local ventilation volume function and the benchmark ventilation volume function, and calculates an integration value of absolute values of ventilation volumes or a maximum value of the absolute values of the difference function as the quantitative value.

Still further, in the image analysis apparatus according to the present invention, the quantification means may be a means that calculates a difference in time to reach a predetermined ventilation volume between the local ventilation volume function and the benchmark ventilation volume function as the quantitative value.

Further, the image analysis apparatus according to the present invention may further include a display control means that visualizes the quantitative value on the three-dimensional images displayed or on two-dimensional images obtained from the three-dimensional images.

Still further, in the image analysis apparatus according to the present invention, the display control means may be a means that visualizes the quantitative value by mapping the quantitative value on each point in the displacement vector field in each of the three-dimensional images or each of the two-dimensional images.

Further, in the image analysis apparatus according to the present invention, the alignment means may be a means that performs the alignment by a non-rigid registration method.

Still further, in the image analysis apparatus according to the present invention, the alignment means may be a means that performs the alignment based on a correlation between the three-dimensional images.

Further, in the image analysis apparatus according to the present invention, the three-dimensional images may be three-dimensional images generated from CT images or MRI images.

Still further, in the image analysis apparatus according to the present invention, the quantification means may be a means that quantifies the difference after normalizing the local ventilation volume function and the benchmark ventilation volume function in a time axis direction.

Further, in the image analysis apparatus according to the present invention, the quantification means may be a means that quantifies the difference after normalizing the local ventilation volume function and the benchmark ventilation volume function by a maximum value of the local ventilation volume function or the benchmark ventilation volume function.

Still further, in the image analysis apparatus according to the present invention, the benchmark ventilation volume function may be a function representing a volume change in the entire lungs of the same subject as that for which the three-dimensional images are obtained, a vital capacity function of the same subject, a function representing a volume change in a partial region of the lungs of the same subject, a ventilation volume function calculated based on many healthy persons, or a ventilation volume function calculated mathematically.

An image analysis method according to the present invention is a method that analyzes, based on a series of three-dimensional images of lungs at different time phases, a three-dimensional distribution of ventilation volume of the lungs, the method including:

extracting a lung region from each of the three-dimensional images;

aligning the lung regions between the series of three-dimensional images and calculating a displacement vector field in the lung region;

calculating a local ventilation volume function representing a temporal change in ventilation volume at each point in the displacement vector field in each of the three-dimensional images based on the displacement vector field; and quantifying a difference between the local ventilation volume function and a benchmark ventilation volume function serving as a reference and calculating a quantitative value representing the difference.

The image analysis method according to the present invention may be provided as a program for causing a computer to perform the image analysis method.

According to the present invention, a lung region is extracted from each of a series of three-dimensional images of lungs at different time phases, the lung regions are aligned between the series of three-dimensional images, and a displacement vector field in the lung region is calculated. Then, a local ventilation volume function at each point in the displacement vector field in each of the three-dimensional images is calculated based on the displacement vector field and a difference between the local ventilation volume function and a benchmark ventilation volume function serving as a reference is quantified and the difference is calculated as a quantitative value. Therefore, by displaying the three-dimensional images in time series order, the three-dimensional lung motion during respiration may be checked. Further, a local abnormality in the lungs with respect to ventilation volume may be confirmed by the quantitative value.

Further, by visualizing the quantitative value on the three-dimensional images, three-dimensional lung motion during respiration may be checked along with local ventilation volumes Further, the quantification of a difference between the local ventilation volume function and the benchmark ventilation volume function after normalizing the functions in a time axis direction or by a maximum value of the local ventilation volume function or the benchmark ventilation volume function allows more accurate quantification of the difference to be made.

BEST MODE FOR CARRYING OUT THE INVENTION

Figure 1:
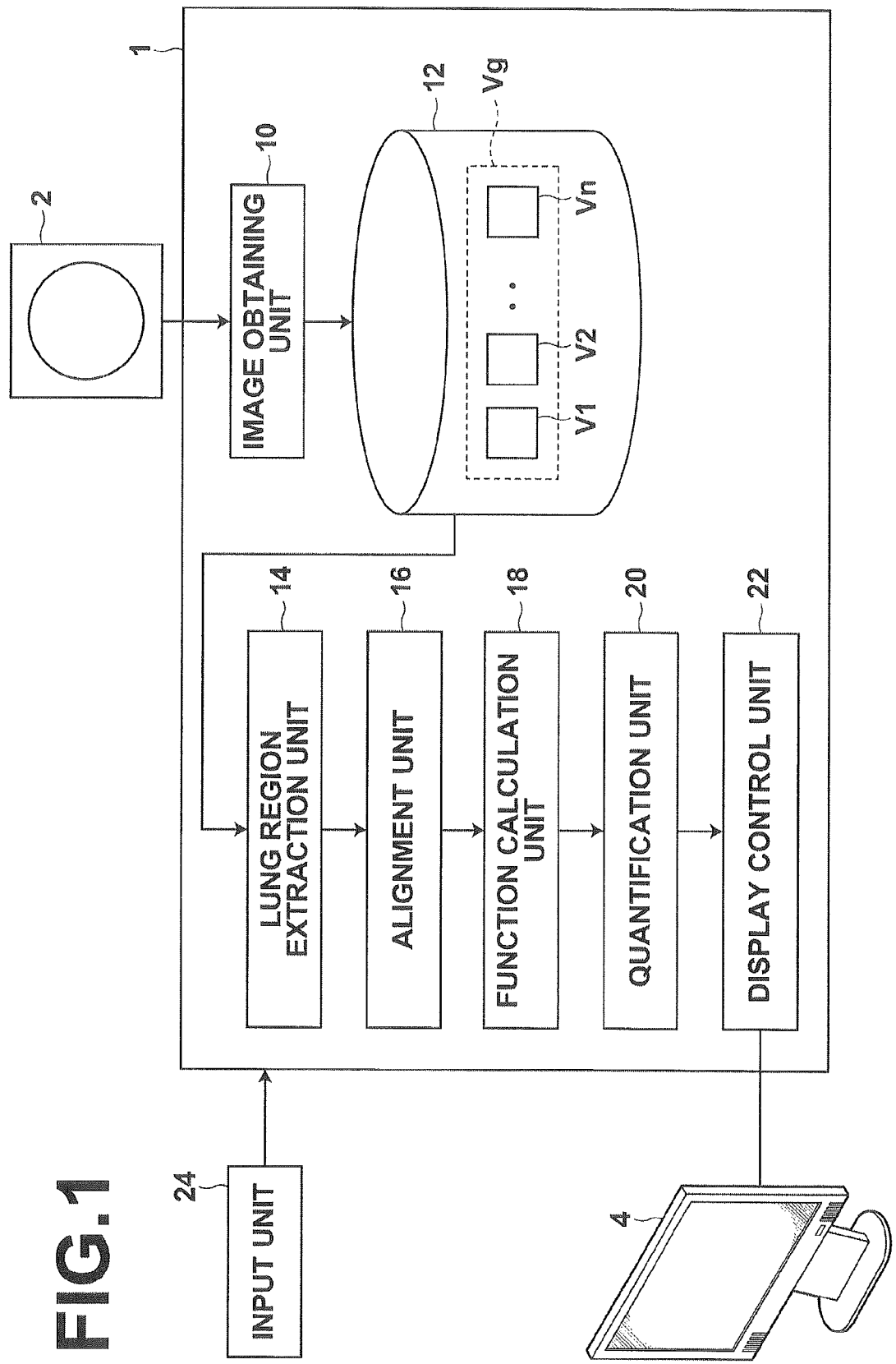
FIG. 1 is a schematic block diagram of an image analysis apparatus according to an embodiment of the present invention, illustrating a configuration thereof.

Hereinafter, embodiments of the present invention will be described with reference to the accompanying drawings. FIG. 1 is a schematic block diagram of an image analysis apparatus according to an embodiment of the present invention, illustrating a configuration thereof. The configuration of the image analysis apparatus 1 shown in FIG. 1 is realized by executing an image analysis program read into an auxiliary storage unit on a computer.

The image analysis program is provided being recorded on a storage medium, such as CD-ROM and the like, or distributed via a network, such as the Internet, and installed on a computer.

The image analysis apparatus 1 according to the present embodiment includes an image obtaining unit 10, a storage unit 12, a lung region extraction unit 14, an alignment unit 16, a function calculation unit 18, a quantification unit 20, a display control unit 22, and input unit 24.

The image obtaining unit 10 has a communication interface function to obtain a three-dimensional image group Vg of a plurality of three-dimensional images Vi (i=1 to n) obtained by imaging a chest region of a subject at a predetermined time interval Δt by a modality 2, such as a multi-slice CT system, a MRI system, or the like. The three-dimensional image group Vg is sent from the modality 2 via a LAN.

Here, the three-dimensional images Vi are obtained by stacking two-dimensional images of a chest region to be diagnosed obtained in order along a direction perpendicular to the cross-sectional face, and generated by superimposing a plurality of tomographic images captured by the modality 2 in the present embodiment. Note that a three-dimensional image obtained with a CT system becomes data in which an absorbed amount of X-ray is stored in each voxel (i.e., pixel position) that forms a grid point in a three-dimensional space, and one signal value (a value representing the absorbed amount of X-ray, if captured by a CT system) is given to each pixel position.

The three-dimensional image group Vg includes a series of three-dimensional images Vi obtained, for example, by imaging a subject at different time phases T1, T2, - - -, Tn separated by a fixed time interval Δt. Preferably, the imaging of the subject is performed in the order of exhaling-inhaling-exhaling or in the order of inhaling-exhaling-inhaling, but the imaging may be performed in the order of exhaling-inhaling or inhaling-exhaling.

Note that auxiliary information defined by DICOM (Digital Imaging and Communications in Medicine) is appended to the three-dimensional images Vi. The auxiliary information may include, for example, an image ID for identifying the three-dimensional image represented by each three-dimensional image vi, a patient ID for identifying the subject, an examination ID for identifying the examination, a unique ID (UID) allocated to each image information, examination date and examination time when the image information was generated, a type of modality used in the examination for obtaining the image information, patient information, such as the patient name, age, gender, and the like, an examination region (imaging region, chest region in the present embodiment), imaging conditions (with or without contrast agent, radiation dose, and the like), and information, such as a series number or a harvest number when a plurality of images was obtained at a time, and the like.

The storage unit 12 is a large capacity storage device such as a hard disk or the like, and the three-dimensional image group Vg is stored. The storage unit 12 includes a plurality of three-dimensional image groups Vg of different subjects (i.e., different patients) or of the same subject imaged at different times.

The lung region extraction unit 14 extracts a lung region from each of the three-dimensional images Vi. As for the method of extracting the lung region, any method may be used, including an method that extracts the lung region by making a histogram of signal values of the respective pixels from the three-dimensional image Vi and performing threshold processing on the lung region, a region growing method based on seed points representing the lung region, and the like. If a lesion area is present near the boundary of the lungs, it is preferable that a concave portion of the lung region which is the lesion area be newly included in the lung region through a curve interpolation using a radius of curvature before and after the concave portion at the boundary of the lung region and extracted as described, for example, in Japanese Unexamined Patent Publication No. 2008-253293.

The alignment unit 16 aligns corresponding pixel positions in the lung region extracted from each three-dimensional image Vi between the three-dimensional images Vi and calculates a displacement vector field in the lung region. More specifically, the alignment is performed by relating corresponding pixel positions between three-dimensional images adjacent in time phase using the method described in V. Boldea et al., "Lung Deformation Estimation with Non-rigid Registration for Radiotherapy Treatment", Proceedings of MICCAI, Vol. 2878, pp. 770-777, 2003 (Reference Document 1), and calculates a displacement vector field in the lung region between the two three-dimensional images adjacent in time phase. The method described in Reference Document 1 performs the alignment of the lung regions extracted from two CT images on a voxel basis using a non-rigid registration method, and a method that obtains a displacement vector field in which the similarity of signal values is maximal and the elastic energy due to deformation is minimal. Note that the alignment method is not limited to the method of Reference Document 1 and the alignment may be performed by a method that calculates a correlation between three-dimensional images adjacent in time phase and obtains a displacement vector field where the correlation becomes minimal.

In the following description, the displacement vector field between two adjacent time phases (Ti to Ti+1) calculated by the alignment is denoted as $D(Ti)(x, y, z)$ in the time between the two time phases. Here, $(x, y, z)$ is the three-dimensional coordinate of each point of the displacement vector field. Further, the cumulative amount of change in the displacement vector field to a specific time Tk is denoted as $F(Tk)(x, y, z)$. The cumulative amount of change $F(Tk)(x, y, z)$ corresponds to the sum of the displacement vector field D(Ti) (x, y, z) obtained at each time phase from t=T1 to t=Tk.

Note that each three-dimensional image Vi may be smoothed before the alignment is performed. More specifically, each three-dimensional image Vi may be smoothed by calculating an average value of signal values at each pixel position using a smoothing filter of a predetermined size (e.g., 3×3×3). When performing the alignment, this may reduce the influence of noise included in the three-dimensional images Vi and a more accurate alignment may be made.

The function calculation unit 18 calculates an amount of capacity displacement of each point in the displacement vector field per unit time as a local ventilation volume P(Ti) (x, y, z) using the displacement vector field D(Ti) (x, y, z) calculated by the alignment unit 16. More specifically, the divergence at each point in the displacement vector field in the lung region is calculated as the local ventilation volume in the lungs, as described in aforementioned Japanese Unexamined Patent Publication No. 2005-028121. The term "local ventilation volume" as used herein refers to a ventilation volume at any partial (local) region in the lungs. In the present embodiment, the local region is formed of one voxel or a plurality of adjacent voxels. The relationship between the divergence at each point in the displacement vector field in the lung region and the local ventilation volume in the lungs may be explained as follows.

That is, the ventilation in the lungs is an incompressible flow of air and the lung parenchyma is deformed by the air flow. The theory of elastic body may be applied to the deformation of the lung parenchyma associated with respiration by regarding the lungs as a porous elastic body. It is known that the local deformation in an elastic body may be expressed using a displacement vector field in a local region and a deformation tensor (3×3 matrix form) and, in particular, if the coordinate axis direction is taken in the main direction of deformation tensor field, the deformation tensor is diagonalized and the trace (sum of the diagonal elements) corresponds to the divergence of the displacement vector. Further, at this time, the volume change rate in the local region may be approximated by the trace of the diagonalized deformation tenor, that is, the change rate of the volume due to deformation can be regarded as corresponding to the dispersion of the displacement vector. Note that in the tissues without any flow of air, such as a lung blood vessel and the like, the divergence is 0 because such tissues may deform but the volume change is negligible.

Figure 2:
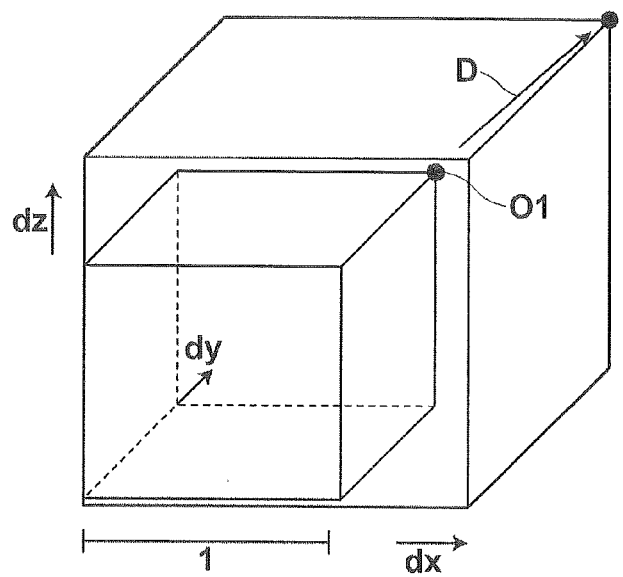
FIG. 2 is a drawing conceptually illustrating a relationship between the divergence of a displacement vector and the volume change due to deformation.

FIG. 2 is a drawing conceptually illustrating the relationship between the divergence of a displacement vector field and the volume change due to deformation. In FIG. 2, D represents a displacement vector field at a point O1 and dx, dy, dz represent small displacements of a unit cube in x, y, z axis directions respectively. At this time, the volume change of the unit cube may be obtained by (1+dx)·(1+dy)·(1+dz)−1 and this can be approximated by dx+dy+dz. Therefore, the volume change rate of the unit cube may be regarded as corresponding to the divergence of the displacement vector field. When an arbitrary vector function is denoted as A (x, y, z) the divergence is generally represented as divA or $\nabla \cdot A$ using a Hamiltonian operator. Here, as the vector function is D(Ti)(x, y, z) in the present embodiment, the divergence divD may be calculated by Formula (1) given below and the calculated divergence divD is the local ventilation volume P(Ti) (x, y, z) at each point in the displacement vector field between certain time phases.

$$divD = \nabla \cdot (t) = \frac{\partial D_x(t)}{\partial x} + \frac{\partial D_y(t)}{\partial y} + \frac{\partial D_z(t)}{\partial x} \quad (1)$$

The function calculation unit 18 further calculates a local ventilation volume function Q(t) (x, y, z) representing a temporal change in ventilation volume by integrating the local ventilation volumes between each time phase with respect to all time phases. The local ventilation volume function Q(t) (x, y, z) during t=T1 to Tk corresponds to the sum of the local ventilation volumes P(t) (x, y, z) during t=T1 to Tk.

The quantification unit 20 quantifies a difference between the local ventilation volume function Q(t) (x, y, z) and a benchmark ventilation volume function V(t) (x, y, z) serving as a reference. The benchmark ventilation volume function will be described first. In the present embodiment, a global ventilation volume function, a vital capacity ventilation function, a partial ventilation volume function, an average model ventilation volume function, or a mathematical model ventilation volume function is used as the benchmark ventilation volume function. Note that these functions are calculated and stored in the storage unit 12 in advance.

The global ventilation volume function represents a volume change of the entire lungs of the same subject as that for which the three-dimensional images Vi are obtained, and may be calculated by volume (capacity) integration of the local ventilation volume function Q(t) (x, y, z) of each point in the displacement vector field within the lung region. The global ventilation volume function represents a temporal change in ventilation volume of the entire lung region of the same subject as that for which the three-dimensional images Vi are obtained.

The vital capacity ventilation function may be obtained by performing spirometry on the same subject as that for which the three-dimensional images Vi are obtained. The vital capacity ventilation function represents a temporal change in ventilation volume obtained by actual measurements with respect to the same subject as that for which the three-dimensional images Vi are obtained.

The partial ventilation volume function represents, when the lung fields of the same subject as that for which the three-dimensional images Vi are obtained are divided into a plurality of regions, a volume change in the partial region and may be obtained by volume integration of the local ventilation volume function Q(t) (x, y, z) of each point in the displacement vector field with respect to each partial region. As the left and right lungs are divided into six regions of upper, middle, and lower regions for diagnosis by a ratio with respect to the entire length of the lungs in the Goddard classification used in the COPD guidelines, each of six regions divided according to the Goddard classification may be regarded as the partial region. Further, the interlobar membrane may be extracted from the lung region to divide the lungs into five leaves and the five regions so obtained may be used as the partial region. Still further, bronchi, lung artery, and lung vein may be extracted from the lung region and a control region of each branch of the bronchi, lung artery, and lung vein may be calculated, and each of the control regions may be used as the partial region. If it is undesirable that the ventilation volume functions are discontinued at the boundary of partial regions, the ventilation volume function with respect to each partial region may be interpolated near the boundary in order to smoothly change the ventilation volume functions at the boundary of the partial regions.

Figure 3:
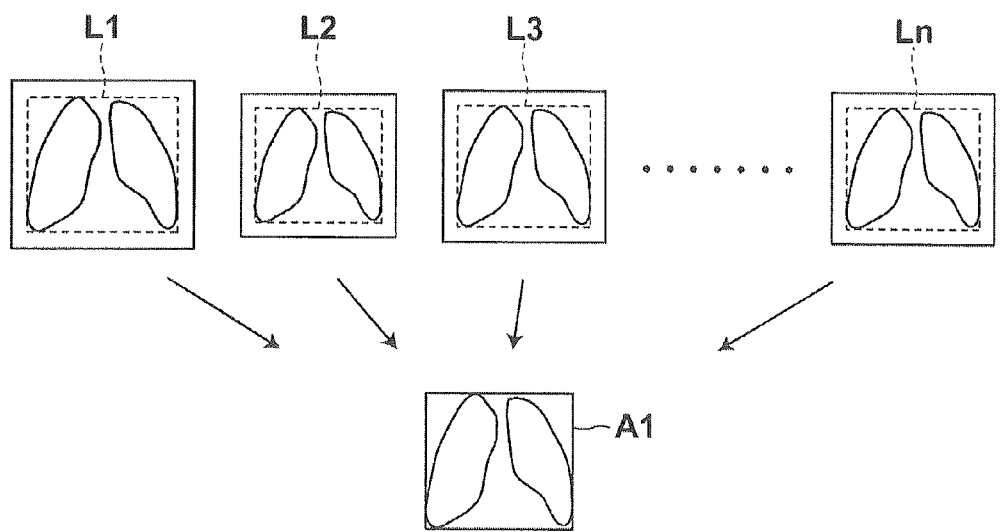
FIG. 3 is a drawing for explaining a calculation of an average model ventilation volume function.

Next, the average model ventilation volume function will be described. FIG. 3 is a drawing for explaining calculation of the average model ventilation volume function. First, local ventilation volume functions are calculated with respect to many healthy persons using three-dimensional images as in above. Here, as the size of the lung region varies between individuals, a local ventilation volume function space A1 having a predetermined size is set and an area Lj (j=1 to m) surrounding the lung region of each individual is normalized such that the size thereof corresponds to the size of the local ventilation volume function space A1. Note that the local ventilation volume function space A1 and the area surround the lung region are cuboid, but they are shown as rectangles in FIG. 3 for explanation purposes. Then, the local ventilation volume function Q(t) (x, y, z) of each point in the displacement vector fields with respect to many healthy persons is mapped to the local ventilation volume function space A1 and an average of local ventilation volumes at each point is calculated. In this case, for an area in the local ventilation volume function space A1 where each point of the displacement vector field is not present, that is, for an area in the local ventilation volume function space A1 where no lung region is present at all, the ventilation volume function of the displacement vector field at a point closest to the area is allocated. Then an arithmetic mean of the local ventilation volume function at each point is calculated and this is used as the average model ventilation volume function. Note that the arithmetic mean of the local ventilation volume function at each point may be smoothed using a smoothing filter of a predetermined size (e.g., 3×3×3). This may reduce the influence of noise and the average model ventilation volume function may be calculated more accurately.

Further, instead of the normalization to the local ventilation volume function space A1, an arrangement may be adopted in which the lung region of one of the many healthy persons is set as the benchmark lung region and lung regions of the other healthy persons may be aligned with respect to the benchmark lung region using the aforementioned non-rigid registration method. In this case, the local ventilation volume function Q(t) (x, y, z) of each point in the displacement vector fields with respect to many healthy persons may be mapped to the benchmark lung region after the alignment, and the average model ventilation volume function may be calculated by calculating an average of the local ventilation volume functions at each point.

The mathematical model ventilation volume function uses a function obtained by approximating the aforementioned average model ventilation volume function by a formula. Otherwise, a lung ventilation volume function calculated from a lung ventilation model simulated in advance may be used as described in R. Werner et al., "Modeling Respiratory Lung Motion—a Biophysical Approach using Finite Element Methods", Proc. of SPIE, Vol. 6916, pp. 69160N-1-69160N-11, 2008 (Reference Document 2) or H. Kitaoka, "A 4D Model Generator of the Human Lung", Forma, Vol. 26, pp. 19-24, 2011 (Reference Document 3). The method described in Reference Document 2 is a method that verifies displacement of the modeled respiratory ventilation volume function from the positions of specific characteristic points extracted from three-dimensional images of a plurality of time phases. The method described in Reference Document 3 is a method that generates an artificial lung model and calculates an average ventilation volume function from the artificial model.

The quantification unit 20 quantifies a difference between the local ventilation volume function Q(t) (x, y, z) and the benchmark ventilation volume function V(t) (x, y, z) and calculates the difference as a quantitative value. In performing the quantification, the quantification unit 20 normalizes the local ventilation volume function Q(t) (x, y, z) and the benchmark ventilation volume function V(t) (x, y, z).

Here, if the benchmark ventilation volume function is a function obtained from the same subject along with the local ventilation volume function, like the global ventilation volume function and the partial ventilation volume function, there is no displacement in a time axis direction between the benchmark ventilation volume function and the local ventilation volume function and the normalization in the time axis direction between the two functions is unnecessary. In the meantime, in performing the quantification, it is important to compare the shapes of the two functions, the local ventilation volume function Q(t)(x, y, z) and the benchmark ventilation volume function V(t) (x, y, z) are normalized by the entire variation. More specifically, the local ventilation volume function Q(t)(x, y, z) and the benchmark ventilation volume function V(t) (x, y, z) are normalized by a maximum Q(t) max and a maximum V(t) max respectively. The normalized local ventilation volume function Q(t) (x, y, z) and benchmark ventilation volume function V(t) (x, y, z) become Q(t) (x, y, z)/Q(t)max and V(t) (x, y, z)/V(t)max respectively.

Figure 4:
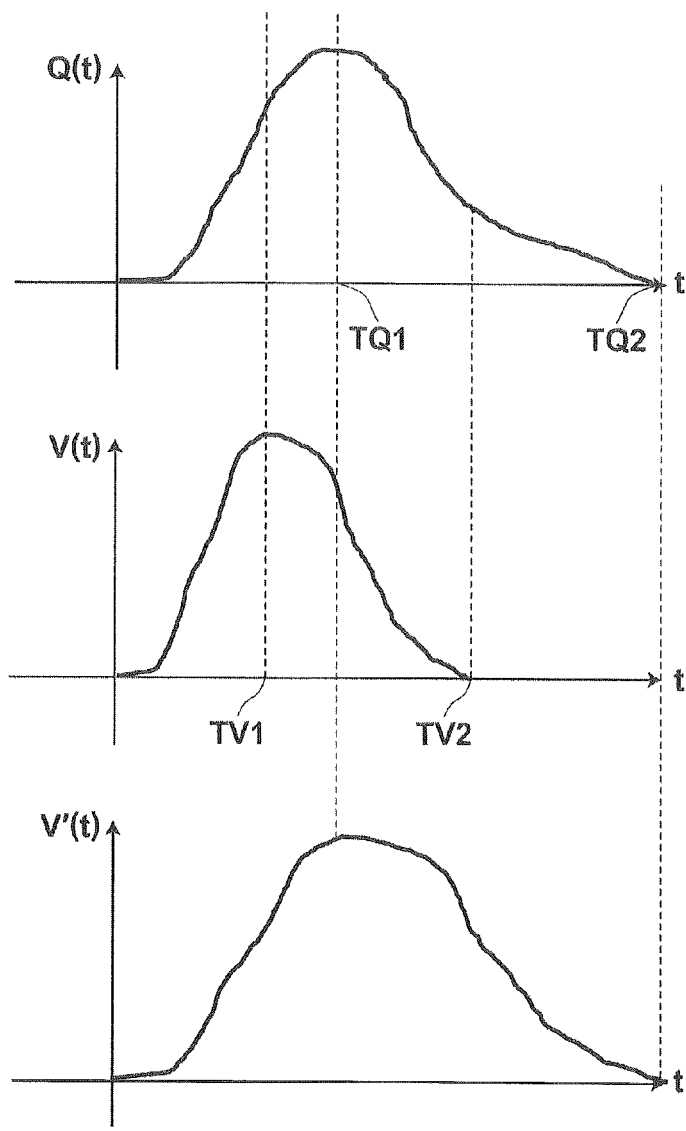
FIG. 4 is a drawing for explaining normalization of a ventilation volume function.

On the other hand, if the benchmark ventilation volume function is the vital capacity ventilation function, the average model ventilation volume function, or the mathematical model ventilation volume function, normalization is required also in a time axis direction of the two functions. Therefore, the normalization is performed with respect to exhalation timing and inhalation timing of the two functions. FIG. 4 is a drawing for explaining normalization of a ventilation volume function. Note that FIG. 4 explains the case where the benchmark ventilation volume function V(t) (x, y, z) is normalized. As illustrated in FIG. 4, the inhalation timing TQ1 and the exhalation timing TQ2 of the local ventilation volume function Q(t) (x, y, z) are shifted respectively from the inhalation timing TV1 and the exhalation timing TV2 of the benchmark ventilation volume function V(t) (x, y, z). Therefore, the benchmark ventilation volume function V(t) (x, y, z) is normalized such that the inhalation timing TV1 and the exhalation timing TV2 of the benchmark ventilation volume function V(t) (x, y, z) correspond respectively to the inhalation timing TQ1 and the exhalation timing TQ2 of the local ventilation volume function Q(t) (x, y, z). Further, the benchmark ventilation volume function normalized in the time axis direction is normalized by the entire variation and the local ventilation volume function Q(t) (x, y, z) is normalized by the entire variation. The normalized local ventilation volume function Q(t) (x, y, z) and benchmark ventilation volume function V(t) (x, y, z) are hereinafter referred to as Q' (t) (x, y, z) and V' (t) (x, y, z) respectively.

Figure 5:
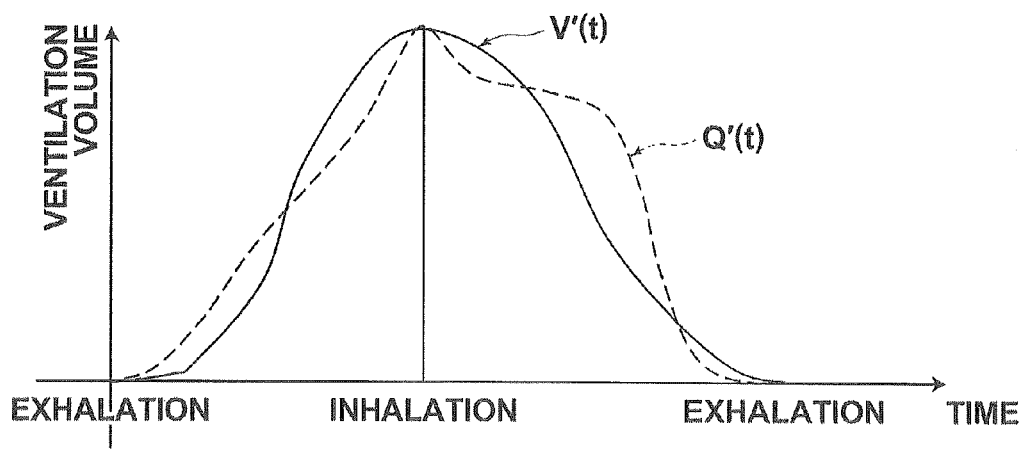
FIG. 5 is a drawing for explaining a comparison between a normalized local ventilation volume function and a normalized benchmark ventilation volume function in a certain region of lungs.
Figure 6:
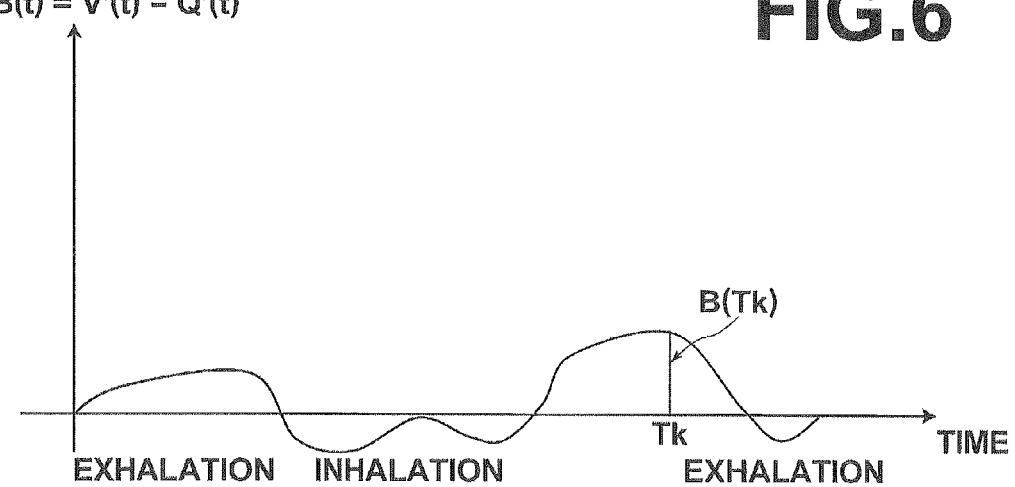
FIG. 6 illustrates a difference function.

Here, if air flows in and out of each region of the lungs normally, the normalized local ventilation volume function and the benchmark ventilation volume function should match. But, in actuality, they do not sometimes match due to influence of a specific disease, influence of gravity, or physiologically normal respiratory motion. FIG. 5 is a drawing for explaining the comparison between the normalized local ventilation volume function and the normalized benchmark ventilation volume function in a certain region of lungs. In FIG. 5, the horizontal axis represents time and the vertical axis represents ventilation volume. Further, the FIG. 5 shows ventilation volumes under the state of exhalation—inhalation—exhalation with the starting time of the exhalation as the reference (i.e., time=0). In diagnosing a lung disease, it is important to confirm the state that the ventilation volumes do not match. Consequently, the quantification unit 20 calculates a difference function B(t) (x, y, z) (=Q' (t) (x, y, z)–V' (t) (x, y, z)), which is a function of difference values between the normalized local ventilation volume function and benchmark ventilation volume function, as a quantitative value. FIG. 6 illustrates a difference function. As illustrated in FIG. 6, the difference function B(t) (x, y, z) shows a difference between the local ventilation volume and benchmark ventilation volume with the passage of time and, more specifically, shows to what extent the ventilation of a local position is delayed from the reference ventilation.

If the benchmark ventilation volume function is the partial ventilation volume function, the difference function may be calculated using the local ventilation volume function of a partial region from which the partial ventilation volume is obtained and the partial ventilation volume function.

Figure 7:
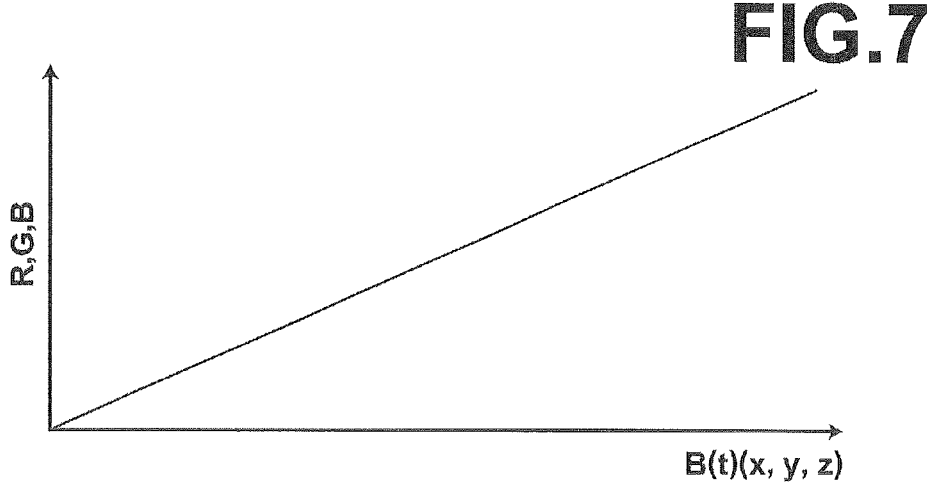
FIG. 7 illustrates a one-dimensional lookup table.

When displaying the three-dimensional image Vi on the display 4, the display control unit 22 displays the difference function B(t) (x, y, z) along with the three-dimensional image Vi. More specifically, the display control unit 22 extracts a lung region from the three-dimensional images Vi and displays a volume rendering image or a surface rendering image (hereinafter, simply VR image) of the lungs. Further, the display control unit 22 mapping displays the difference function B(t) (x, y, z) on the surface of the lung VR image. That is, the display control unit 22 displays a signal at a pixel position on the lung surface at each time phase by converting to a color according to the difference function B(t) (x, y, z) corresponding to the pixel position. The color conversion is performed using, for example, a one-dimensional lookup table in which the value of difference function B(t) (x, y, z) is set to the horizontal axis and the color (R, G, B) is set to the horizontal axis, as illustrated in FIG. 7. Although only one lookup table is shown in FIG. 7, three lookup tables for R, G, B are actually provided.

Figure 8:
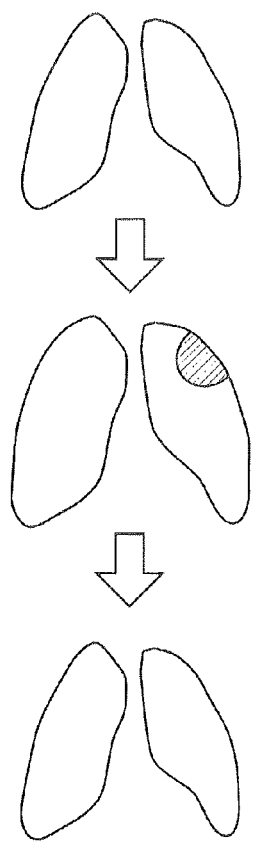
FIG. 8 is a drawing for explaining display of lung VR images.

The display control unit 22 converts a signal value of each pixel on the lung surface to a display pixel value of each of R, G, B with reference to the lookup tables. Then, the display control unit 22 displays the converted lung VR images on the display 4 in time series order. FIG. 8 is a drawing for explaining the display of lung VR images. As illustrated in FIG. 8, a portion of the lungs having an abnormal ventilation amount is displayed on the display 4 along with a deformed state of the lungs according to the respiration. Note that three-dimensional images of lungs are displayed on the display 4, but the lungs are represented by two-dimensional images in FIG. 8 for explanation purposes. Further, a region where an abnormal ventilation volume is locally observed under inhalation is indicated by the slashes in FIG. 8.

The input unit 24 includes known input devices, such as a keyboard, a mouse, and the like.

Figure 9:
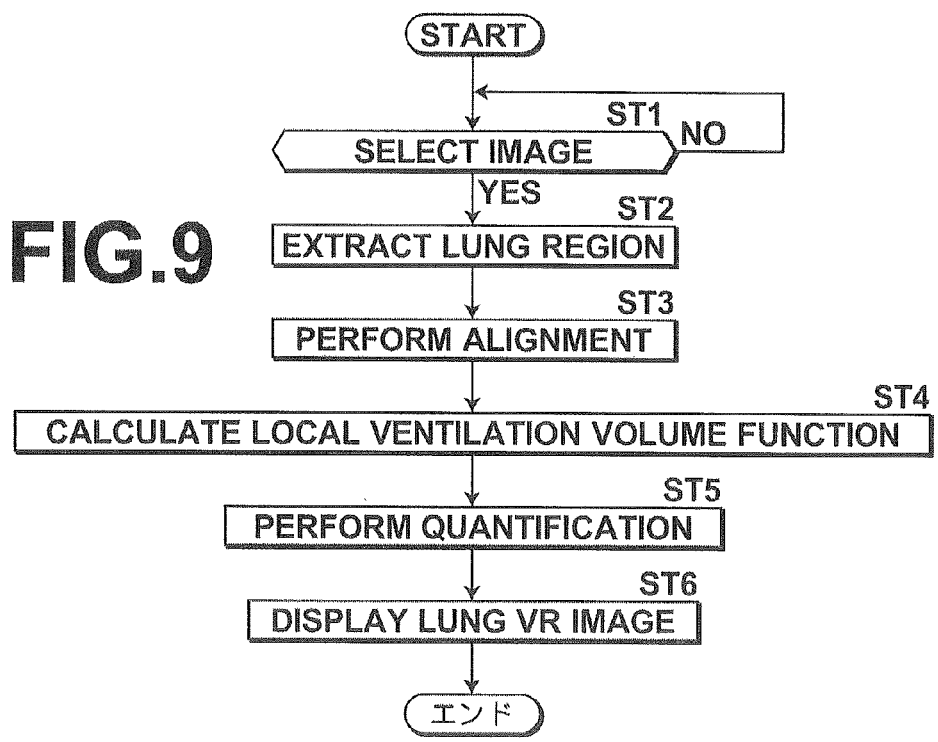
FIG. 9 is a flowchart of processing performed in the present embodiment.

Next, the processing performed in the present embodiment will be described. FIG. 9 is a flowchart of processing performed in the present embodiment. It is assumed that the plurality of three-dimensional images Vi of lungs has been obtained by the image obtaining unit 10 and stored in the storage unit 12. When three-dimensional images to be displayed are selected by an operator by operating the input unit 24 (step ST1 YES), the lung region extraction unit 14 reads out the selected three-dimensional images Vi from the storage unit 12 and extracts a lung region from each of the three-dimensional images Vi (step ST2) Then, the alignment unit 16 aligns pixel positions corresponding to the lung region extracted from each of the three-dimensional images Vi between the three-dimensional images Vi (step ST3). This calculates a displacement vector field at each time phase of the three-dimensional images Vi.

Then, the function calculation unit 18 calculates a local ventilation volume function Q(t) (x, y, z) representing a temporal change in ventilation volume at each point of the displacement vector field (step ST4). Next, the quantification unit 20 calculates a difference function B(t) (x, y, z), which is a function of difference values between the local ventilation volume function and the benchmark ventilation volume function by performing quantification, as a quantitative value representing a difference between the local ventilation volume function and the benchmark ventilation volume function (quantification, step ST5). Further, the display control unit 22 displays lung VR images on which the difference function is mapped on the display 4 in time series order (step ST6), and the processing is completed.

In lung diseases, such as cancer, bronchial asthma, lung infarction, and the like, there may be a portion of the lungs that has become stiff where the alveoli do not work properly. But diagnosis of such a portion is difficult by simply observing the image. Therefore, there exists an inspection method that calculates the ventilation volume as in the spirometry, but the ventilation volume alone simply shows what amount of air the lungs have finally taken in and lung motion state cannot be known.

In the present embodiment, the difference function that represents the difference between the local ventilation volume function and the benchmark ventilation volume function is mapped on the three-dimensional images and displayed in time series order. This allows three-dimensional motion of the lungs during respiration to be checked and a local abnormality of the lungs to be confirmed through comparison with the surrounding state by the mapped difference function. If a portion of a lung field has become completely stiff and no air ventilation is performed, the ventilation volume is 0 in principle. In the present embodiment, it is possible to confirm, in a region having a ventilation volume greater than a predetermined value, whether or not the ventilation volume is normal or abnormal through comparison with the ventilation volumes of surrounding regions. In addition, it is possible, if the ventilation volume is abnormal, to visually confirm as to what extent it is abnormal. Therefore, by following up the state of the lungs regularly using the present embodiment, the diagnosis as to whether or not the condition of the disease is aggravated may be made easily.

Here, in the case where the global ventilation volume function is used as the benchmark ventilation volume function, if air is taken in uniformly over the entire lungs for respiration, the local ventilation volume function of each region of the lungs should have a similar function shape to that of the benchmark ventilation volume function. If the lungs have a certain disease, however, the local ventilation volume function of the region having the disease has a function shape different from that of the benchmark ventilation volume function. Consequently, a local abnormality of the lungs may be detected by setting the global ventilation volume function as the benchmark ventilation volume function.

In the meantime, in the case where the global ventilation volume function is used as the benchmark ventilation volume function, if the number of sampled points, i.e., points for which the displacement vector fields are calculated is small, the ventilation volume may not be estimated accurately. On the other hand, the spirometry may easily obtain a ventilation volume function of a continuous time, so that the benchmark ventilation volume function may be calculated accurately and easily.

Further, if one benchmark ventilation volume function is calculated from the entire lung region and the difference between the benchmark ventilation volume function and the local ventilation volume function is set as the quantitative value, the difference in ventilation volume between each region due to the gravity or the difference in ventilation volume between each region which should be essentially judged normal may not be distinguished and, as a result, a region having such a difference may possibly be detected as an abnormal region. Therefore, by setting the partial ventilation volume function as the benchmark ventilation volume, and quantifying a difference between the partial ventilation volume function and the local ventilation volume function for each region, only a region having a local abnormality may be detected.

Further, by setting the average model ventilation volume function calculated in advance using healthy persons or the mathematical model function, it becomes easier to identify an abnormal region and it is possible to identify an abnormal region without being influenced by the bias in the ventilation volume due to the gravity of the lung fields or by the bias physiologically present in the ventilation volume.

In the embodiment described above, the difference function B(t) (x, y, z) is mapped on the surface of the lungs in the lung VR images but the difference function B(t) (x, y, z) may be mapped on cross-sections provided by cutting the lungs in the lung VR images.

Further, in the embodiment described above, the difference function B(t) (x, y, z) is calculated as quantitative values, but the absolute maximum value |B(Tk)| of the difference function B(t) (x, y, z) shown in FIG. 6 may be calculated as the quantitative value. The absolute maximum value |B(Tk)| shows a maximum difference in ventilation volume of a region where the difference function B(t) (x, y, z) is calculated with respect to the normal region. Further, the time Tk where the absolute value |B(t) (x, y, z)| becomes maximum may be set as the quantitative value. The time Tk shows the time when a difference in ventilation volume of a region where the difference function B(t) (x, y, z) is calculated becomes maximum with respect to the normal region. Note that, for the time, a specific time point, for example, the exhalation starting time may be used as the reference. Further, the integration value of the difference function B(t) (x, y, z) may be used as the quantitative value. In this case, the quantitative value represents the sum of the differences of a region where the difference function B(t) (x, y, z) is calculated with respect to the normal region.

Figure 10:
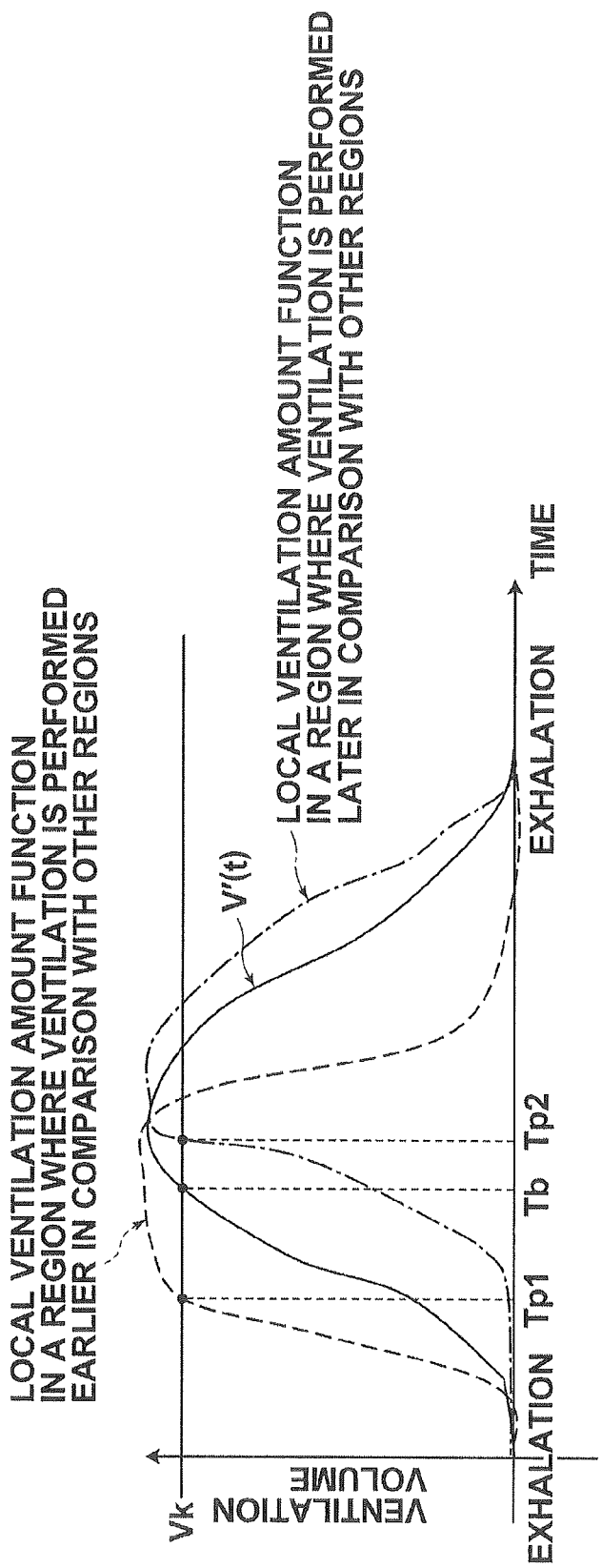
FIG. 10 is a drawing for explaining another example of quantification between a local ventilation volume function and a benchmark ventilation volume function.

Further, for a region where an air ventilation is performed earlier in comparison with the other regions, a time Tp1 where the local ventilation volume function reaches a given ventilation volume Vk comes earlier that a time Tb where the benchmark ventilation volume function reaches the given ventilation volume, as illustrated in FIG. 10. In contrast, for a region where an air ventilation is performed later in comparison with the other regions, a time Tp2 where the local ventilation volume function reaches a given ventilation volume comes later that the time Tb where the benchmark ventilation volume function reaches the given ventilation volume. Therefore, a value of difference between a time from a certain reference time (e.g., time when exhalation is started as shown in FIG. 10) to the time when the predetermined ventilation value Vk is reached in the local ventilation volume function and a time to the time when the predetermined ventilation value Vk is reached in the benchmark ventilation volume function (e.g., Tp−Tb) may be calculated as the quantitative value. In this case, if the quantitative value of a certain region becomes negative, it is known that the air ventilation in the region is performed earlier in comparison with the other regions, while if the quantitative value becomes positive, it is known that the air ventilation in the region is performed later in comparison with the other regions.

Figure 11:
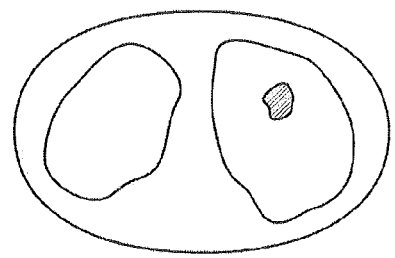
FIG. 11 is a drawing illustrating the state in which a quantitative value is overlaid on a lung region in a MRP cross-section.

In the case where such a quantitative value, which is not a difference function, is calculated, the quantitative value may be mapped on the lung VR images. In this case, the color on the lung surface does not change with the passage of time, but the lung motion state and a region having an abnormal value of ventilation volume may be confirmed. Further, in this case also, the quantitative value may be mapped on cross-sections provided by cutting the lungs in the lung VR images. Still further, as illustrated in FIG. 11, the quantitative value may be overlay displayed on the lung region in the MPR cross-section of the three-dimensional image Vi. Note that the overlay displayed portion in FIG. 11 is indicated by the slashes in FIG. 11.

What is claimed is:

1. An image analysis apparatus that analyzes, based on a series of three-dimensional images of lungs at different time phases, a three-dimensional distribution of ventilation volume of the lungs, the apparatus comprising:
a lung region extraction unit that extracts a lung region from each of the three-dimensional images;
an alignment unit that aligns the lung regions between the series of three-dimensional images and calculates a displacement vector field in the lung region;
a function calculation unit that calculates a local ventilation volume function representing a temporal change in ventilation volume at each point in the displacement vector field in each of the three-dimensional images based on the displacement vector field; and
a quantification unit that quantifies a difference between the local ventilation volume function and a benchmark ventilation volume function serving as a reference and calculates a quantitative value representing the difference.

2. The image analysis apparatus as claimed in claim 1, wherein the quantification unit calculates a difference function representing a difference between the local ventilation volume function and the benchmark ventilation volume function as the quantitative value.

3. The image analysis apparatus as claimed in claim 1, wherein the quantification unit calculates a difference function representing a difference between the local ventilation volume function and the benchmark ventilation volume function, and calculates an integration value of absolute values of ventilation volumes or a maximum value of the absolute values of the difference function as the quantitative value.

4. The image analysis apparatus as claimed in claim 1, wherein the quantification unit calculates a difference in time to reach a predetermined ventilation volume between the local ventilation volume function and the benchmark ventilation volume function as the quantitative value.

5. The image analysis apparatus as claimed in claim 1, wherein the apparatus further comprises a display control unit that visualizes the quantitative value on the three-dimensional images displayed or on two-dimensional images obtained from the three-dimensional images.

6. The image analysis apparatus as claimed in claim 5, wherein the display control unit visualizes the quantitative value by mapping the quantitative value on each point in the displacement vector field in each of the three-dimensional images or each of the two-dimensional images.

7. The image analysis apparatus as claimed in claim 1, wherein the alignment unit performs the alignment by a non-rigid registration method.

8. The image analysis apparatus as claimed in claim 1, wherein the alignment unit performs the alignment based on a correlation between the three-dimensional images.

9. The image analysis apparatus as claimed in claim 1, wherein the three-dimensional images are generated from CT images or MRI images.

10. The image analysis apparatus as claimed in claim 1, wherein the quantification unit quantifies the difference after normalizing the local ventilation volume function and the benchmark ventilation volume function in a time axis direction.

11. The image analysis apparatus as claimed in claim 1, wherein the quantification unit quantifies the difference after normalizing the local ventilation volume function and the benchmark ventilation volume function by a maximum value of the local ventilation volume function or the benchmark ventilation volume function.

12. The image analysis apparatus as claimed in claim 1, wherein the benchmark ventilation volume function is a function representing a volume change in the entire lungs of the same subject as that for which the three-dimensional images are obtained, a vital capacity function of the same subject, a function representing a volume change in a partial region of the lungs of the same subject, a ventilation volume function calculated based on many healthy persons, or a ventilation volume function calculated mathematically.

13. An image analysis method that analyzes, based on a series of three-dimensional images of lungs at different time phases, a three-dimensional distribution of ventilation volume of the lungs, the method comprising:

extracting a lung region from each of the three-dimensional images;

aligning the lung regions between the series of three-dimensional images and calculating a displacement vector field in the lung region;

calculating a local ventilation volume function representing a temporal change in ventilation volume at each point in the displacement vector field in each of the three-dimensional images based on the displacement vector field; and quantifying a difference between the local ventilation volume function and a benchmark ventilation volume function serving as a reference and calculating a quantitative value representing the difference.

14. A non-transitory recording medium on which is recorded a program for causing a computer to perform an image analysis method that analyzes, based on a series of three-dimensional images of lungs at different time phases, a three-dimensional distribution of ventilation volume of the lungs, the program causing the computer to perform the steps of:

extracting a lung region from each of the three-dimensional images;

aligning the lung regions between the series of three-dimensional images and calculating a displacement vector field in the lung region;

calculating a local ventilation volume function representing a temporal change in ventilation volume at each point in the displacement vector field in each of the three-dimensional images based on the displacement vector field; and quantifying a difference between the local ventilation volume function and a benchmark ventilation volume function serving as a reference and calculating a quantitative value representing the difference.

* * * * *